United States Patent [19]

Delmulle et al.

[11] Patent Number: 4,546,645
[45] Date of Patent: Oct. 15, 1985

[54] MEASURING DEVICE FOR THE MOISTURE CONTENT OF GRANULAR MATERIALS

[75] Inventors: Jean P. Delmulle, Hauville; Bernard Torchet, Blois, both of France

[73] Assignee: L'Etat Francais représenté par le Ministère de l'Urbanisme et du Logement, Laboratoire Central des Ponts et Chaussees, Paris, France

[21] Appl. No.: 496,625

[22] Filed: May 20, 1983

[30] Foreign Application Priority Data

May 26, 1982 [FR] France ................. 82 09168

[51] Int. Cl.⁴ ............................................. G01R 27/26
[52] U.S. Cl. .................................... 73/74; 324/61 P
[58] Field of Search ............. 324/61 P, 61 R; 73/73; 361/280, 284, 285, 286; 15/256.51

[56] References Cited

U.S. PATENT DOCUMENTS

| | | | |
|---|---|---|---|
| 2,848,667 | 8/1958 | Rolfe | 361/280 |
| 3,348,313 | 10/1967 | Urmenyi | 324/61 R |
| 3,748,686 | 7/1973 | Winterburn et al. | 15/256.51 |
| 3,783,781 | 1/1974 | Grommek | 15/256.51 |
| 3,950,698 | 4/1976 | Wochnowski | 324/61 R |
| 4,154,522 | 5/1979 | Ikesue | 15/256.51 |
| 4,278,935 | 7/1981 | Ihara et al. | 324/61 P |

*Primary Examiner*—Charles Frankfort
*Assistant Examiner*—David R. Schuster
*Attorney, Agent, or Firm*—Weingarten, Schurgin, Gagnebin & Hayes

[57] ABSTRACT

Capacitative device for measuring the moisture content of granular or powder materials, particularly materials in motion on a conveyor belt or in a pipe comprising a capacitative probe provided with at least two electrodes separated by an insulating zone and in contact with the material being examined, a support frame for the capacitative probe, and high frequency oscillator circuit associated with the electrodes in order to supply an alternating voltage of a frequency variable with the moisture content. The probe, which has a cylindrical body may be rotated by a motor and comprises cleaning scrapers mounted on the frame which cooperate with the body of the probe when the latter is rotating.

11 Claims, 5 Drawing Figures

MEASURING DEVICE FOR THE MOISTURE CONTENT OF GRANULAR MATERIALS

BACKGROUND OF THE INVENTION

The present invention relates to a measuring device for the moisture content of granular or powder materials. It relates particularly to such measurement of materials in movement on a conveyor belt or in a pipe. The device is of the type comprising a capacitative probe furnished with at least two electrodes separated by an insulating zone and in contact with the material to be studied, the probe having a cylindrical body, a frame for supporting the capacitative probe, and a high frequency oscillator circuit associated with the electrodes in order to supply an alternating voltage of frequency variable with the moisture content.

It is already known to use capacitative probes for measurement of the moisture content of materials, particularly of materials in the form of granulates, such as materials serving for the formation of concrete objects or of soils. Thus, French Pat. No. 2,062,078 describes a solid capacitative sensor of prismatic shape installed permanently in the midst of the material of which it is desired to measure the moisture content. This known capacitative sensor is associated with a connecting cable of high frequency quality for supplying the sensor with alternating current of a frequency comprised between 10 and 100 MHz.

French certificate of addition No. 2,192,711 also describes a capacitative sensor of moisture content of the aforesaid type, in which the measuring cell is at least partly conical and is associated with the means adapted to convert the capacitative variation of the sensor into a variation in the frequency of the electrical alternating signal delivered by the sensor.

The capacitative sensors of known types are fairly well adapted to measurements in situ, for which the measuring probe is anchored to a fixed position in a floor, for example, or to measurements of moisture content of material without fines. These capacitative sensors have on the other hand drawbacks when it is a matter of measuring the moisture content of certain granular materials, particularly materials possessing fines, when these materials are in motion on a conveyor belt or in a pipe and pass in contact with the capacitative probe on the walls of which are placed the measuring electrodes. In fact, in this case, there often occurs a clogging of certain particles of the material which remain stuck to the body of the probe. Errors of measurement then ensue so that these probes operate poorly in practice.

GENERAL DESCRIPTION OF THE INVENTION

It is an object of the present invention to overcome the aforesaid drawbacks and to provide a measuring device for the moisture content of granular or powder materials which is efficient even in the case of materials having fines and is particularly adapted to the measurements of moisture content carried out on materials in motion such as flows in pipes or hoppers or over conveyor belts.

Accordingly the device according to the invention comprises in addition means for driving in rotation the probe with respect to the frame intermittently at regular intervals during a limited period of time and cleaning means mounted on the frame and cooperating with the cylindrical body of the probe during the rotary movements of the latter, and wherein a measurement of the moisture content of the material under examination is effected constantly when the probe is in resting position.

More particularly, the cleaning means comprise at least one scraper supported by an arm connected to the frame, and applied against the surface of the cylindrical body of the probe.

According to an advantageous embodiment of the invention, the cleaning means comprise several distinct scrapers aligned along a generator of the cylindrical body of the probe and each supported independently by an arm connected to the frame.

Preferably, each scraper is connected to the frame through an articulated arm and flexible elements are associated with the articulation of the arm to transmit to the corresponding scraper a support pressure on the body of the probe.

The cylindrical body of the probe may be extended forwards by a frustoconic portion. In this case, at least one scraper supported by an arm connected to the frame is applied against the surface of the frustoconic portion of the probe.

The probe is mounted so as to be rotatable on two sets of bearings arranged at the lower portion of two uprights of the frame and means for driving the probe in rotation with respect to the frame comprise a motor-reducing unit arranged in the frame above the probe, and capable of driving the latter in rotation through its rear portion.

The upright of the frames supporting the forward portion of the probe has advantageously a shell or bullet-shaped nose arranged along the axis of the probe.

According to a particular embodiment the device comprises a first central electrode constituted by an incurved conducting plate arranged longitudinally at the periphery of the insulating cylindrical body of the probe in the lower portion of this body when the probe is in resting position, and a second lateral electrode comprising two incurved conducting plates arranged longitudinally at the periphery of the cylindrical body of the probe at a short distance on each side of the first central electrode.

The device comprises electronic circuits arranged inside the cylindrical body of the probe and connected on the one hand to the electrodes of the probe by fixed connections and on the other hand to external sockets by means of a rotary contact.

According to the invention, the electronic circuits arranged inside the cylindrical body of the probe comprise a high frequency oscillator and frequency divider circuits, associated with matching circuits in order to permit the supply of a low frequency signal on said rotary contact, whilst high frequency signals are applied to the electrodes of the probe.

More particularly, the electronic circuits arranged inside the cylindrical body of the probe are supplied with a continuous voltage comprised between about 3.5 and 8 volts and preferably close to 5 volts, the frequency of the oscillator is comprised between about 10 and 100 MHz and preferably comprised between 35 and 45 MHz and the output frequency of the low frequency signal which is a function of the moisture content of the material examined is comprised between about 5 and 10 kHz and preferably close to 7 kHz.

Other features and advantages of the invention will emerge from the description of a particular embodiment which follows, given purely by way of non-limiting illustration, with reference to the accompanying drawings.

BRIEF DESCRIPTION OF THE DRAWINGS

In the drawings:

FIG. 4 is a half-view from above of the embodiment of the device of FIG. 3 showing the self-cleaning device associated with the probe and FIG. 5 shows the diagram of the electronic circuits arranged inside the body of the probe.

DESCRIPTION OF PREFERRED EMBODIMENTS

Figure 1:
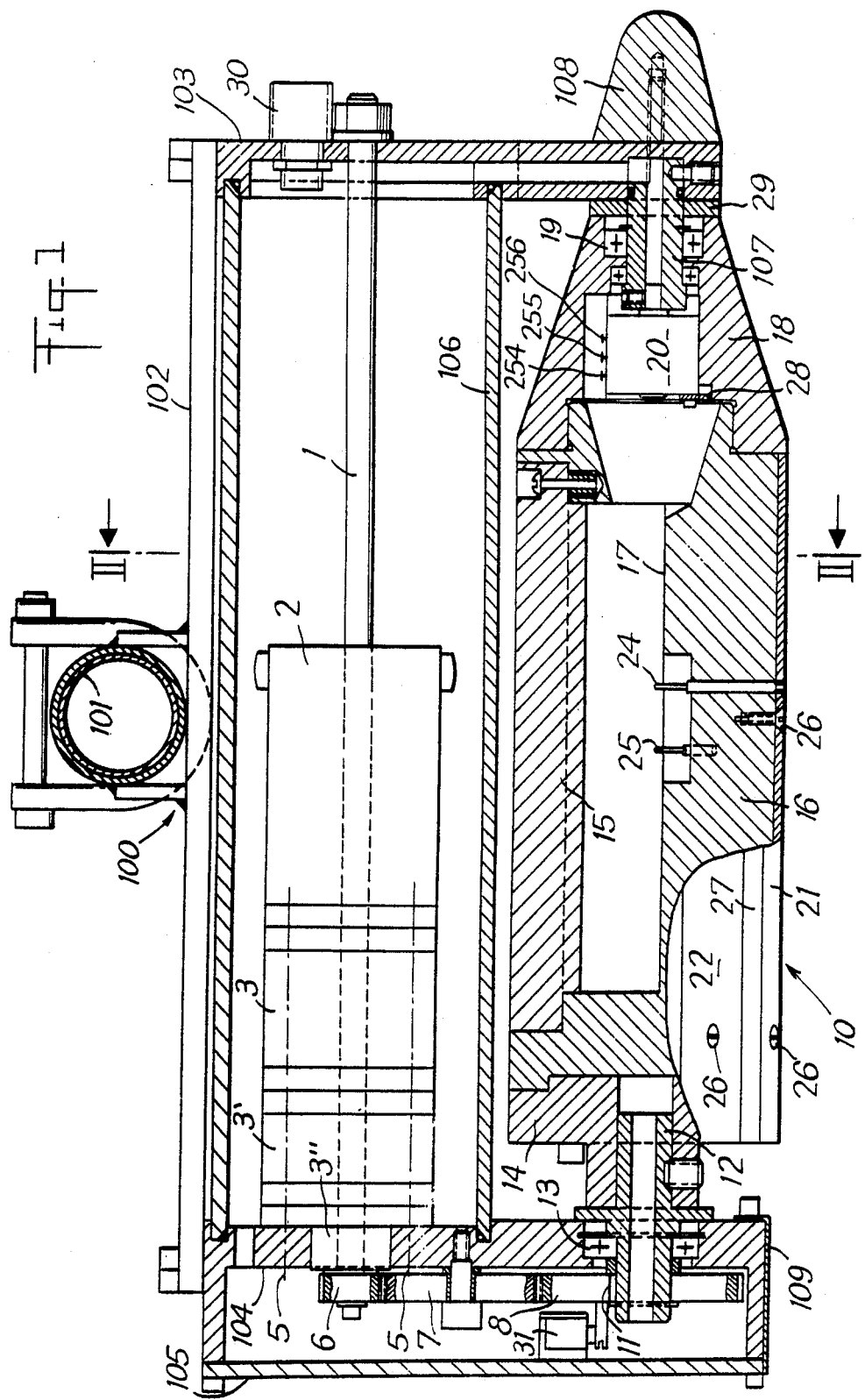
FIG. 1 is an axial sectional view of an embodiment of the measuring probe according to the invention, mounted on a frame, but the self-cleaning device of the probe being omitted.

In FIG. 1 is seen the mechanical diagram of a capacimetric probe adapted to the measurement of the moisture content of the granular or powder material which may be constituted by a material serving for the manufacture of bituminous or hydraulic mixtures or again by an agricultural or food product in granular form.

The measurement of the moisture content of a material is important. For example, in the case of bituminous mixtures, there are used drum-dryer-coaters and, with such machines, the bitumen content, which is an essential characteristic of a bituminous mixture, is directly connected with the flow rate of the dry granulates entering the drum, hence to a knowledge of their moisture content.

Reduction in the consumption of powder material, cement particularly, in the case of the manufacture of gravel treated with hydraulic binders, necessitates also the knowledge of the moisture content of the materials entering the mixer of the installation. Not knowing how to measure the moisture content of the mixture, mostly applied in a layer, to the supply loader of the drum or of the mixer, it is important to know how to measure the moisture content of the materials on the belt of each means for measuring out the granulates.

The principle of measuring the moisture content of the material flowing on a conveyor belt or in a pipe or in a hopper is as follows. The probe is immersed in the stream of material. The shape of the probe is preferably formed so as to enable very good flow of material along the walls on which are located the metal electrodes. The material sliding between the electrodes constitutes the dielectric of the capacitor which is an element of an electronic oscillator placed inside the body of the probe. The frequency of the oscillator is inversely proportional to the moisture content. The frequency signal is transmitted to an external processing unit which converts it into voltage and, taking into account the calibration effected at the start, enables the registration of information on the moisture content of the examined material.

One of the essential problems connected with the use of capacimetric probes for the measuremnt of moisture content of materials in flow, is constituted by the clogging which occurs regularly on the probe. In fact, as soon as a portion of the material remains stuck to the body of the probe, the measure carried out no longer gives reliable data as regards the moisture content of the material flowing by.

According to the invention, the capacitative measuring probe 10 is not mounted fixedly on a frame 100, but on the contrary is associated with drive means such as an electric motor 2, in order to be able to be rotated around its axis. Cleaning means 40 (FIGS. 3 and 4) associated with the frame 100 and with the probe 10 enable automatic cleaning of the surface of the probe when the latter is rotated.

Thus, the device according to the invention enables at the same time continuous measurement instantaneously during the intervals of times of measurement where the probe is in its resting position, and effective cleaning of the body of the probe during the brief periods of cleaning where the probe is in rotation and the measurements are inhibited. The cleaning periods may be repeated in predetermined manner at regular intervals.

The measuring device of FIG. 1 is adapted to be dipped into a current of material flowing from right to left in the longitudinal direction of the probe 10. The probe 10 is held in position by a frame 100 which comprises essentially a transverse support tube 101, an upper horizontal plate of the frame 102, fixed to the tube 101, and vertical uprights 103, 104 fixed to the upper plate of the frame 102 and connected to one another by tie-rods 1. The uprights 102, 104 constitute thus forward and rear fronting flanges.

An electric motor 2 associated with reducing gears 3, 3' and having an outlet flange 3" incorporated in the rear vertical wall 104 of the frame, is arranged in the vicinity of the upper portion of the frame 100, inside a protective tube 106 placed between the upper plate 102 and the probe 10. The motor-reducing unit 2,3,3' fixed to the vertical wall 104 by screws 5 is superposed to the probe 10, being substantially parallel to the latter. A gear train 6,7,8 positioned behind the vertical wall 104 of the frame, and protected by a rear cover 105, transmits through a cotter 11 to a shaft 12 fast to the probe 10 the drive motion communicated by the motor reducing gear unit 2,3,3', when the latter is in operation.

Figure 2:
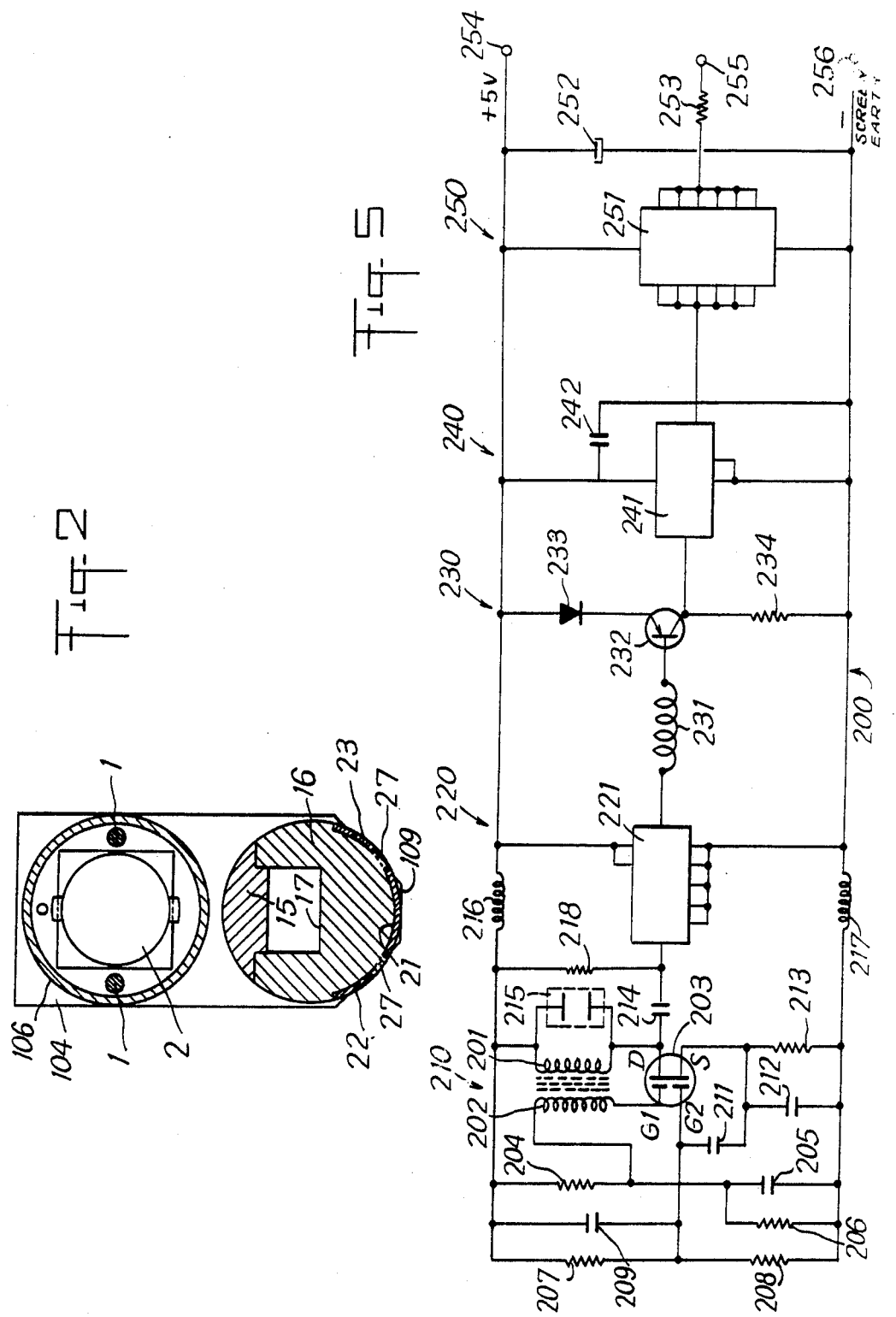
FIG. 2 is a sectional view along the plane II—II of FIG. 1.

The measuring probe 10 has a cylindrical body prolonged at its forward portion by a frustoconic portion 18. The body of the probe 10 is essentially cylindrical in shape with a circular cross-section and is seen to be in two main parts 15, 16 defining an internal cavity 17 (FIGS. 1 and 2). The body of the probe thus comprises a base body 16 surmounted by a removable cap 15 giving access to the cavity 17. The rear axle 12 of the probe 10 is mounted in a terminal part 14 connected to the rear of the base body 16. A frustoconic portion 18 fast to the cylindrical body 15, 16 of the probe extends the latter forward around an axle 107 fast to the front upright 103 of the frame 100. The probe 10 is mounted on bearings 13, 19 which are located respectively in the rear upright 104 of the frame and around an axle 107 fixed directly to the front upright 103.

A protective washer of rubber is interposed between the fixed front upright 103 and the frustoconic head 18 of the probe. A shell shaped nose 108 is in addition fixed to the front upright 103 in extension of the axle of the probe, in order to facilitate the flow of the material to be examined towards the frustoconic head 18 of the probe and the cylindrical body 16. In the rear of the frame, the upright 104 is itself completed by a foot whose lower surface bears a chafing plate 109.

As can be seen in FIGS. 1 and 2, the body 16 of the probe 10 bears at its peripheral portion metal electrodes 21,22,23 fixed by screws 26 to the body 16 formed, in the same way as the cover 15, the rear terminal portion 14 and the frustoconic head 18, of an insulating material, for example moulded material. The electrodes 21,22,23 in the shape of incurved plates, for example of stainless steel are anchored in the body 16 of the probe and have an outer surface which forms a portion of the cylindrical surface of the body of the probe 10. A lower electrode 21 is arranged at the lower middle portion of the body of the probe placed in its resting position. The electrode 21 extends in the longitudinal direction of the probe to the limit of the frustoconic portion 18. Two electrode portions 22,23 are themselves arranged symmetrically on each side of the lower electrode 21 being seperated from the latter by portions 27 of insulating material of the same dimensions. Connections 24,25 link respectively the lower central electrode 21 which constitutes a first electrode of a capacitor and the lateral electrodes 22,23 which are at the same electrical potential and constitute a second capacitor electrode, to electronic circuits positioned in the cavity 17. A rotary contact 20 or collector with three tracks positioned inside the frustoconic head 18 permits the three output terminals 254, 255, 256 of the electronic circuits 200 positioned in the cavity 17 and hence fast to the probe 10, to be connected to a connector 30 mounted on the front upright 103 of the frame. The connector 30 thus enables on the one hand the inlet of the supply wire of the electric motor 2 positioned in the protective tube 106 and on the other hand the necessary connections with the circuits 200 associated with the capacitative probe 10.

The motor reducing gear unit 2,3,3' drives the probe 10 in rotation during the periods of cleaning the probe. The rotary movements of the probe 10 thus permit automatic cleaning of the cylindrical bodies 16, 15 of the probe and of the associated electrodes 21,22,23 due to the presence of scrapers 46 (FIGS. 3 and 4) which remove all possible deposits of material on the peripheral surface of the probe.

Figure 3:
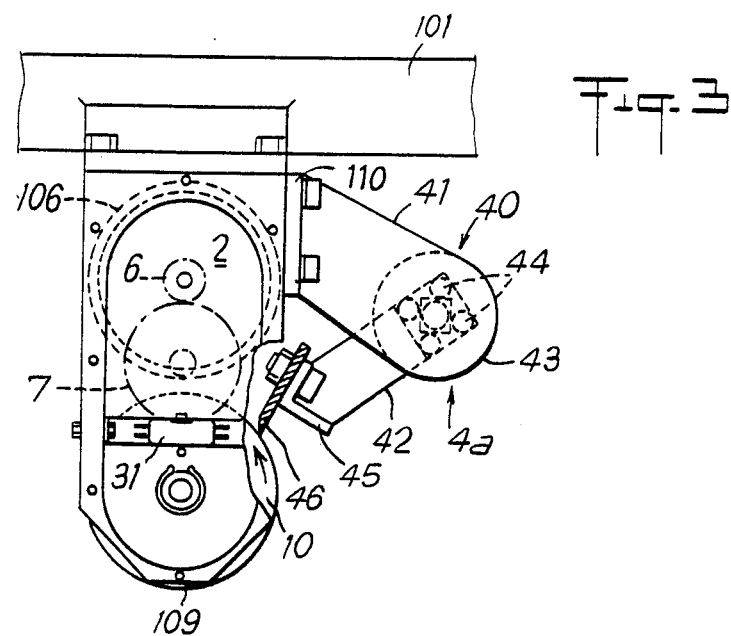
FIG. 3 is a rear view, with the cover removed, of the embodiment of FIG. 1, showing also the self-cleaning device associated with the probe and with the frame.
Figure 4:
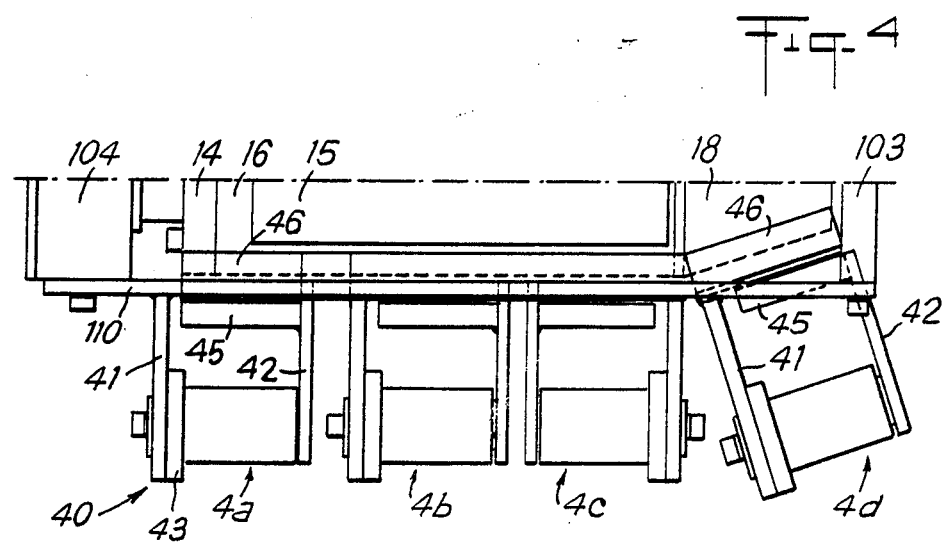

The cleaning unit 40 of the probe 10 will be described in more detailed manner with reference to FIGS. 3 and 4. FIG. 4 shows the employment of four individual cleaning units 4a, 4b, 4c, 4d each comprising a scraper 46 cooperating with the surface of the cylindrical body 15, 16 or of the frustoconic head 18 of the probe 10. The four individual cleaning units 4a to 4d are similar to one another and only one unit will be described in detail. The three cleaning units 4a, 4b, 4c, have scrapers whose active surface is parallel to the axis of the probe whilst the cleaning unit 4d is inclined with respect to the axis of the probe so that the active surface of the scraper 46 of this fourth cleaning assembly corresponds to a generator of the frustoconic head 18 of the probe.

Each individual cleaning unit 4a to 4d comprises a fixed arm 41 connected to a longitudinal transverse member 110 of the frame fixed to the vertical uprights 103, 104.

An articulation 43 connects a second arm 42 to the fixed arm 41 and incorporates flexible elements 44 which exert on the second arm 42 a force providing the scraper 46 which is mounted by means of a blade holder 45 at the end of the arm 42, a supporting pressure against the body of the probe 10.

The scrapers 46 may be of metal and do not interfere with the electrical capacitance measurements since they remain essentially parallel to the electrodes 21,22,23 and during the periods of measurement are in contact with the upper portion of the body 15, 16 of the probe or of the head 18 which are of insulating material and do not carry electrodes. The cleaning unit 40 of the probe 10 is in fact, arranged for the main part above the probe 10 (FIG. 3). This cleaning unit cannot either disturb appreciably the stream of material flowing along the probe 10.

The periods that the probe 10 is placed in rotation, which correspond to cleaning phases during which the scrapers 46 can remove over the whole peripheral surface of the probe, including on the electrodes 21,22,23, particles of material which would be deposited thereon, may comprise for example 1,2 or 3 probe revolutions and have a total duration of the order of some seconds. In a way, the cleaning may be fully effective, without the period of interruption of the measurement carried out with the probe being troublesome, taking into account the usual speeds of flow of the materials. The cleaning operations may or may not be repeated at regular intervals. The duration of the intervals between cleaning operations, which corresponds also to the periods of actual measurement, is selected as a function of the nature of the material examined and of its clogging tendency, as well as a function of the speed of flow of the material on the conveyor belt. These intervals may be, for example, of the order of some minutes. The actuation of the placing of the probe 10 in rotation and of its stopping, preferably in a resting position which is always identical, is done by acting directly on the drive motor 2 which may, for example, be a d.c. motor which is short-circuited during the periods of rest of the probe corresponding to the measuring periods. This periodic short-circuiting of the motor 2 may be done entirely automatically by means of an external time delay circuit, (not shown) which forms part of a control or regulation system. A micro-switch 31, or a position detector 28 associated with the motor 2 or with the probe 10 may, for example, ensure the control of the stopping of the motor 2 and hence of the probe 10 in the resting position after a predetermined number of revolutions of the probe 10 in order to control the end of each cleaning cycle. Taking into account the gear reduction effected between the motor 2 and the probe 10, the stopping of the motor 2 can result also in an instaneous stopping of the probe 10.

The electronic circuits 200 cooperating with the electrodes 21,22,23 to enable the formation of a signal representing the degree of humidity of the material analysed will now be described with reference to FIG. 5. In this Figure, by the reference 215 is denoted the measuring cell constituted by the electrode 21 and the electrode 22 or 23 of the probe 10. This measuring cell 215 constitutes a capacitor whose capacitance varies as a function of the nature of the material present between the electrodes and of the moisture content of this material. By means of a prior calibration carried out for a given material, the cell 215 enables the development of the moisture content of the material to be followed since the variations of the latter are manifested by variations in the capacitance of the cell 215. The measuring cell 215 is combined with an H F oscillator circuit 210 which supplies an alternating voltage whose frequency varies as a function of the capacity of the cell 215 and hence as a function of the moisture content of the material analysed.

The structure itself of the H F oscillator 210 is of known type. According to the invention, the H F oscillator 210 is however associated with frequency dividing stages 220, 240 and with impedance matching stages 230, 250 so as to provide at the output of the terminal 255 a low frequency signal, for example of the order of 7 kHz. It follows that the connection between the electronic circuits 200 arranged in the cavity 17 of the rotary probe 10 and the display, processing or regulating devices fast to the frame 100 may be effected by means of a slip ring 20, without disturbances appearing. The connecting cables between the slip ring 20 of the probe 10 and the display or processing equipment are themselves practically insensitive to the environment in which the measuring device is placed and may have considerable length, several tens of meters, for example, which permit the use of measuring probes in combination with a central control and regulation station. On the other hand, the capacitative probes of the prior art required the use of high frequency cables very sensitive to disturbances and thus introduced limitations in the use of capacitative measuring probes.

The oscillator 210 must at the same time preserve a narrow phase margin of little dependance on frequency in the range of operation (which is preferably comprised between 30 and 50 MHz) and especially ensure a sufficient amplitude of oscillation and a stable level to trigger the frequency divider system. For this, the stabilized supply voltage of the circuit 200 is advantageously selected between 3.5 and 8 volts and is preferably in the neighbourhood of 5 volts. In addition, the gain control element 203 of the oscillator is advantageously constituted by a double grid field effect MOS transistor. By way of example, the model 40673 of the RCA company may be used which has a high gain (30 dB), high transconductance and permits large gain regulation (50 dB).

The oscillator 210 comprises two coupled inductance coils 201 and 202. The first inductance coil 201 is mounted in parallel with the measuring cell 215 whilst the second inductance coil 202 is connected on the one hand to the first grid of the transistor MOS 203 and on the other hand to the middle point of a divider bridge constituted by the resistors 204 and 206 which are mounted in series between the positive supply pole of the assembly and ground. The divider bridge 204, 206 has high internal resistance and in the absence of oscillations polarises the grid G1 of the transistor 203 positively. The operating point of the transistor 203 is defined by the internal resistance of the divider bridge 204, 206 and by the potential of the grid G2 of the transistor 203, established by the divider bridge constituted by the resistors 207 and 208. The resistor 213 polarises the source of the transistor 203. The assembly in parallel of the first inductance coil 201 and the measuring cell 215 is connected between the positive supply of the assembly and the drain of the transistor 203. The capacitors 209, 205, 211 and 212 are high frequency cut-off capacitors. The capacitor 209 is connected in parallel with the resistor 207, the capacitor 205 is mounted in parallel to the resistor 206, the capacitor 211 is connected between the grid G2 and the source of the transistor 203 and the capacitor 212 is mounted in parallel to the resistor 213.

The operation of the oscillator 210 is as follows. In the absence of oscillations, the grid G1 is polarised positively by the divider bridge 204, 206 as has been previously indicated. When the oscillations are developed in the coil 202, due to the fact that in the example selected the transistor 203 is of the N depletion type, the current between the grid G1 and the source S is generated at the positve peaks of the oscillations, which polarises negatively the grid G1, thus reducing the gain of the transistor and consequently the amplitude of the oscillations. The reduction in the amplitude of the HF signal at the ends of the second coil 202 reduces the negative potential of the grid G1, and produces an increase in the gain of the transistor 203. The level of the oscillations is thus regulated.

The output of the oscillator stage 210, on the drain of the transistor 203, is connected through a linking capacitor 214 to a first frequency divider stage 220 comprising a circuit 221 for dividing by 11 in ECL technology (that is to say emitter coupling logic circuit). The circuit 221 is associated with two inductance coils 216, 217 interposed between the external terminals of the stablised supply 254, 256 and the oscillator stage 210. A bias resistor 218 is also interposed between the input of the circuit 221 and the positive supply terminal of the oscillator circuit 210.

An impedance matching stage 230 follows the first divider stage 220 and comprises a series circuit constituted by a diode 233, the emitter-collector junction of a transistor 232 and a resistor 234, connected between the supply terminals 254 and 256. An inductance coil 231 in addition mounted between the output of the frequency divider stage 220 and the base of the transistor 232.

A second frequency divider stage 240 is connected following the matching stage 230 and comprises an integrated circuit CMOS 241 associated with a capacitor 242. This stage may effect, for example, a division by 512 of the frequency of the signal emerging from the matching stage 230.

A last impedance matching stage 250 can comprise an integrated circuit 251, an output resistor 253, as well as a capacitor 252 for filtering the stabilized supply and may be mounted at the output of the second divider stage 240. Thus, at the output terminal 255 of the electronic circuit 200 placed in the probe 10, an LF signal is available whose frequency is a function of the degree of humidity of the material in which the probe is immersed, and which is insensitive to external interference. A frequency-voltage conversion may then be carried out in a device located at a distance from the measuring unit constituted by the probe 10, its rotating means 2 to 8, its cleaning device 40 and its frame 100. In fact, the transmission line of the signals situated between the ring contact 20 and the connector 30 or between the connector 30 and the processing or regulation unit (not shown) no longer introduces the disturbances inherent in the prior art devices. In addition, due to the fact of the periodic and effective cleaning of the probe 10, the signals transmitted from the terminal 255 correspond well to the real condition of the material flowing along side the probe 10.

We claim:

1. Device for measuring the moisture content of at least one of a granular and a powder material, particularly materials in movement on a conveyor belt or in a pipe, of the type comprising a capacitative probe provided with at least two externally mounted electrodes separated by an insulating zone and in contact with the material being examined, the said probe having a cylindrical body, a support frame for the capacitative probe, and a high frequency oscillator circuit associated with the electrodes in order to provide an alternating voltage of frequency variable with the moisture content, said device further comprising means for rotating the probe with respect to the frame intermittently at predetermined regular intervals for a limited time and cleaning means mounted on the frame and cooperating with the cylindrical body of the probe during the rotary movements of the latter, to remove material which has adhered to the probe, and means for measuring the moisture content of the material examined continously when the probe is in a resting position between said predetermined intervals of rotation for cleaning.

2. Device according to claim 1, wherein the cleaning means comprise at least one scraper supported by an arm connected to the frame and applied against the surface of the cylindrical body of the probe.

3. Device according to claim 1, wherein the cleaning means comprise several distinct scrapers aligned along a generator of the cylindrical body of the probe and each supported independently by an arm connected to the frame.

4. Device according to claim 3, wherein each scraper is connected to the frame through an articulated arm and wherein flexible elements are associated with the articulation of the arm to transmit to the corresponding scraper a supporting pressure on the body of the probes.

5. Device according to claim 1, wherein the cylindrical body of the probe is extended forwards by a frustoconic portion and wherein at least one scraper supported by an arm connected to the frame is applied against the surface of the frustoconic portion of the probe.

6. Device according to claim 1, wherein the probe is mounted so as to be rotatable on two sets of bearings arranged at the lower part of two uprights of the frame and wherein the rotary drive means of the probe with respect to the frame comprise a motor-reducing unit arranged in the frame above the probe and capable of rotating the latter through its rear portion.

7. Device according to claim 5, wherein the upright of the frame supporting the forward portion of the probe has a shell-shaped nose arranged along the axis of the probe.

8. Device according to claim 1, comprising a first central electrode constituted by an incurved conducting plate, arranged longitudinally to the periphery of the insulating cylindrical body of the probe in the lower portion of this body when the probe is in resting position, and a second lateral electrode comprising two incurved conducting plates arranged longitudinally to the periphery of the cylindrical body of the probe at a short distance on each side of the first central electrode.

9. Device according to claim 8, comprising electronic circuits arranged inside the cylindrical body of the probe and connected on the one hand to the electrodes of the probe through fixed connections and on the other hand to outer sockets by means of a rotary contact.

10. Device according to claim 9, wherein the electronic circuits arranged inside the cylindrical body of the probe comprise a high frequency oscillator and frequency divider circuits associated with matching circuits in order to permit the supply of a low frequency signal on said rotary contact, whilst the high frequency signals are applied to the electrodes of the probe.

11. Device according to claim 10, wherein the electronic circits arranged inside the cylindrical body of the probe are supplied with a continuous voltage comprised between 3.5 and 8 volts and preferably close to 5 volts, wherein the oscillator frequency is comprised between about 10 and 100 MHz and preferably comprised between 35 and 45 MHz and wherein the output frequency of the low frequency signal which is a function of the moisture content of the material examined is comprised between about 5 and 10 kHz and preferably close to 7 kHz.

* * * * *